United States Patent [19]
Folden

[11] Patent Number: 5,536,258
[45] Date of Patent: Jul. 16, 1996

[54] ANTIBACTERIAL MEDICAL TUBING CONNECTOR

[75] Inventor: Thomas I. Folden, Alamo, Calif.

[73] Assignee: Fresenius USA, Inc., Walnut Creek, Calif.

[21] Appl. No.: 196,974

[22] Filed: Feb. 14, 1994

[51] Int. Cl.⁶ ..................................... A61M 5/32
[52] U.S. Cl. .................... 604/265; 604/905; 604/283
[58] Field of Search .................... 604/264, 265, 604/283, 905; 285/331, 355, 390, 423; 215/344, 329

[56] References Cited

U.S. PATENT DOCUMENTS

| | | | |
|---|---|---|---|
| 802,383 | 10/1905 | Fenn | 215/329 |
| 928,055 | 7/1909 | Johnson et al. | 285/331 |
| 2,258,066 | 10/1941 | Oyen | 285/331 |
| 3,707,240 | 12/1972 | Wilson | 215/41 |
| 4,551,146 | 11/1985 | Rogers | 604/283 |
| 5,049,139 | 9/1991 | Gilchrist | 604/265 |
| 5,176,415 | 1/1993 | Choksi | 285/331 |
| 5,330,235 | 7/1994 | Wagner et al. | 285/81 |

Primary Examiner—Randall L. Green
Assistant Examiner—Chalin Smith
Attorney, Agent, or Firm—Davis, Graham & Stubbs

[57] ABSTRACT

An antimicrobial tubing connector for medical procedures, especially for extracorporeal connections as in peritoneal dialysis and hemodialysis tubing sets. A male portion includes a central tube surrounded by a sleeve radially spaced apart from the central tube to define an annular space. A mating female portion includes a tubular body which receives the central tube of the male portion and which is received by the annular space. A set of O-ring seals and mating threads produces a secure fluid-tight connection. An antimicrobial agent such as silver is deposited on one or more of several surfaces, preferably by a durable process such as ion assisted deposition, to prevent touch contamination. Either or both of the male and female portions may be capped with a separate cap, which may also receive the antimicrobial agent.

7 Claims, 3 Drawing Sheets

ANTIBACTERIAL MEDICAL TUBING CONNECTOR

FIELD OF THE INVENTION

The present invention relates to the field of connectors for extracorporeal medical tubing. Such extracorporeal medical tubing is used in dialysis procedures such as peritoneal dialysis and hemodialysis and in a variety of other medical procedures. Extracorporeal procedures are to be distinguished from intracorporeal procedures and uses such as prosthetic implants, urinary catheters and other implantable catheters, shunts and cannulation devices.

BACKGROUND OF THE INVENTION

Many modern medical procedures require the use of tubing sets of varying complexity to withdraw fluid from a patient, or to administer fluid to a patient, or to do both. Such procedures include intravenous feeding, blood transfusions and blood processing, and both peritoneal dialysis and hemodialysis. Typically, a catheter is temporarily or semipermanently implanted in the patient such as by cannulating a vein in the case of hemodialysis or a catheter is implanted in a peritoneal cavity in the case of peritoneal dialysis. The catheter extends from the implant site to outside the body, where it is connected in some manner to the appropriate tubing set necessary for the procedure that is to be performed.

The configuration and complexity of tubing sets are vastly different depending upon the particular medical procedure for which they are designed and also depending in the manufacturer of the other extracorporeal elements used in the procedure. For example, a hemodialysis tubing set is much different from a peritoneal dialysis tubing set because of the different nature and requirements of hemodialysis as compared to peritoneal dialysis, and a peritoneal dialysis tubing set made by one manufacturer for use with its peritoneal dialysis cycler machine may be much different from a peritoneal dialysis tubing set made by another manufacturer for use with the other manufacturer's peritoneal dialysis cycler machine.

In hemodialysis, the patient's blood is cleansed by drawing it out of the patient though a catheter and passing it through an artificial kidney. The artificial kidney includes a semi-permeable membrane which removes impurities and toxins by a process of diffusion. The purified blood is then returned to the patient. A hemodialysis tubing set is used to transport the blood between the catheters and the artificial kidney. Patients in hemodialysis treatment typically require treatment several times a week for several hours each time.

In peritoneal dialysis, a peritoneal dialysis solution is infused into the patient's peritoneal cavity and allowed to reside there for a "dwell time" during which blood impurities diffuse through the peritoneal membrane into the dialysis solution. The dialysis solution with the collected impurities is then removed from the peritoneal cavity and discarded. In Continuous Ambulatory Peritoneal Dialysis ("CAPD") the infusion of dialysis solution into and out of the peritoneal cavity is accomplished throughout the day while the patient goes about a fairly normal routine. In Intermittent Peritoneal Dialysis ("IPD") large amounts of dialysis solution (up to 40 liters) are cycled through the patient's peritoneal cavity over a 4 to 24 hour period. In Continuous Cycling Peritoneal Dialysis ("CCPD") the dialysis treatment is more or less continuous, with dwell times of 3 to 4 hours at night. Then, throughout the waking time of the patient, a single dose of dialysis solution is retained within the patient.

In both IPD and CCPD an automated dialysis apparatus operates in generally the same manner. The dialysis solution and "tubing administration set" or simply "tubing set" is integrated with the valving, heating and control functions associated with the automated apparatus. In many of the systems, premeasured amounts of dialysis solution are either pumped or delivered by gravity flow to a heating station. At the heating station the solution is warmed to body temperature in order to prevent the uncomfortable sensation of introducing room temperature or cooler solution into the peritoneal cavity. The warmed solution is then allowed to enter the patient via a catheter implanted in the patient's peritoneal cavity. After a period of time (the "dwell period"), the solution is drained from the patient into a spent solution container.

In IPD, a large amount of solution is cycled in this manner over a relatively short period of time. Once treatment is completed, the patient is unencumbered for at least a few days. A disadvantage is the large amount of dialysis solution that must be utilized. Bags cumulating to at least 40 liters of solution can be difficult to lift for a patient in a weakened condition.

In CCPD and CAPD methods, the same efficiency of results is obtained by increasing the dwell time of the dialysis solution within the peritoneal cavity. The total amount of solution required can therefore be significantly reduced. The obvious disadvantage, is that there is no "down time" for the treatment.

One of the significant items of expense in peritoneal dialysis of all types is the tubing set. Tubing sets vary widely depending on the type of peritoneal dialysis with which they are used and the brand of cycling equipment with which they are used, but all of them have a cost that is significant, especially when one considers that they are used between several times a week and several times a day for years. Tubing sets must be sterile, and so they are normally used once and then discarded. Thus, for example, a tubing set that costs only ten dollars becomes a fairly major expenditure for a patient that receives dialysis once a day, if that dialysis continues for years as it very often does.

Many of the tubing sets used with these dialysis procedures or with other medical procedures involving extracorporeal treatment of fluid, use releasable connectors. For example, a hemodialysis patient or a peritoneal dialysis patient will often have a semi-permanent implanted catheter in the vascular system or peritoneal cavity, respectively, which extends to outside the patient. The exterior end of the catheter is capped with a removable cap, or is attached to a tubing segment which in turn is capped with a removable cap. It is very important that these ends and caps be antiseptic to prevent the transmission of disease, especially since many of these patients are already in frail health. The connections must also be mechanically strong and secure to prevent accidental disconnection during the procedure.

For CAPD connectors in particular, the connectors need to be secure and to provide an anti-bacterial effect in the connector. During CAPD, a certain quantity of sterile dialysis fluid is brought from a plastic bag through a tubing system into the peritoneal cavity. After a period of some time, the fluid is transferred from the cavity back to a receiving bag, possibly the same bag. In the meantime, an osmotic equilibrium is accomplished between the waste substances accumulated in the blood of the uraemic patient and the dialysis fluid. By replacing the dialysis fluid with fresh dialysis fluid after several hours, one repeatedly removes a portion of the accumulated waste substances from the blood. Because the dialysis fluid is changed four or five times a day, thousands of connections and disconnections of dialysis bags may be necessary per year. It is absolutely necessary to carry out a sterile connecting and disconnecting procedure. Since the dialysis fluid does not include white blood cells, it is clear that any infectious agents such as bacteria introduced during the connecting procedure, even if there are very few, may multiply unhindered inside the peritoneal cavity of the patient. The problem is compounded by the fact that CAPD treatment often takes place in the patient's non-sterile home and is performed by the patient himself. It is believed that about 60% of CAPD patients suffer from peritonitis within two years after starting treatment.

Other medical treatments may lead to infection less often than CAPD; however, it is still desirable that contamination be held at a minimum. If infectious agents are introduced into the bloodstream during the administration of intravenous fluids or medication, for example, they normally come in contact with white blood cells which strongly counteracts the infection. However, there is a considerable number of patients suffering from a serious reduction in the number or the immunological activity of white blood cells, such as some cancer patients and acquired immune deficiency patients. The introduction of a single bacterium into the body of this group of patients can cause dangerous infections. Various types of connector assemblies attempt to address these problems, but none is perfect.

In a barrier connector assembly of the prior art, both sides of the connector are provided with a deformable barrier. Before connecting the two sides, the barriers are first brought into contact with each other, after which the fixation points of these barriers will not change their mutual position. One of the connectors comprises a telescopically movable penetration tube which is pushed through both barriers and the front end is slid into the other connector. An example of this type of connector assembly is disclosed in U.S. Pat. No. 4,334,551. In coupling the connectors, a sterile connection might be achieved if both barriers have been sprayed beforehand with a sterilizing liquid. However, there is the risk that the penetration tube after penetrating the first barrier, pushes away the second barrier. Then, unsterile air can pass into the resulting space between the barriers. Also, during the disconnection procedures the barriers may be pulled loose from each other by the retracting penetration tube so that unsterile air is sucked between the barriers to contaminate the outside of the penetration tube.

Other commercial attempts at minimizing environmental and touch contamination of a connector apparatus requires the patient to remove povidone iodine antiseptic sponges from a container, to separately remove sterile gauze sponges from another container or envelope, to apply the swab dressing to the spike connector site and to place the gauze sponge around the dressing and then to peel the backing off, and to tape and separately apply it around the dressing and gauze sponges to hold them in place around the connection. Thus, not only must the patient make the tubing connection, inserting the male or spike portion of the connection, but the patient must then immediately manually carry out the several described steps to establish and maintain an antiseptic connection of the connector while the connector remains exposed to the atmosphere. Although the components of the connector are provided in a kit, the components nevertheless require considerable handling.

The difficulties in attempting to utilize antiseptic sponges are addressed in U.S. Pat. No. 4,402,691 through the use of a firm plastic protection enclosure barrier device for surrounding the connection site and providing the site with an antiseptic barrier. The barrier device—sometimes also identified as a clam shell approach—is comprised of a contoured plastic housing formed by mating cavity halves joined along a hinge line, and an absorbent member contained within the interior of the housing in a sealing tab attached to one of the housing halves for holding the two halves together when folded along the hinge line. In use, the absorbent member has antiseptic solution applied to the member and the housing is positioned to surround the connection site and is sealed in place to form a surrounding protective area barrier in seal.

Another prior art attempt in solving patient contamination in CAPD applications is provided in U.S. Pat. No. 4,432,764 which describes an antiseptic end cap for catheters in order to provide antiseptic catheter fittings.

Another antibacterial protective cap for connectors is provided in U.S. Pat. No. 4,440,207. A protective cap for the connector which securely receives and provides an antibacterial effect to the connector is provided wherein at least a portion of the protective cap interior is lined with an absorbent material which retains an antiseptic. The connector covered by the protective cap is thus placed in an anti-bacterial environment made possible by contact of the connector with the antiseptic-retaining absorbent material or from migration of the antiseptic or both.

Yet another attempt to avoid or to minimize the danger of peritoneal infections in CAPD procedures is presented by U.S. Pat. No. 4,810,241. An ambulatory dialysis system connector includes a cylinder containing a disinfecting solution which continuously bathes the male and female connectors of a tube during use. A highly absorbent material is packed in the cylinder and saturated with a disinfectant to bathe the male and female connectors. A connection is provided by a male fitting on the end of a tube connected to a container of dialysate fluid or in an abdominal opposing tube. The male connector is inserted into the female connector through the cylinder containing the absorbent material saturated with the disinfectant. The absorbent material is packed such that the male connector contacts the absorbent material during insertion to disinfect the opposing end simultaneously while connection is being made. Once the dialysate fluid is delivered to the patient through the connector, the tube may be pulled off the outer end of the male connector to remove the empty containers. The male connector is then sealed and capped.

In the field of implantable medical devices such as catheters, shunts and prostheses, there is a body of prior art on using bactericide metallic coatings to prevent infection. One metallic coating that has proven to be effective in such applications is silver. The term "oligodynamic" was coined in the eighteenth century to describe the remarkable antimicrobial properties of highly diluted silver in water. Later work confirmed these properties and led to the use of silver preparations as topical antimicrobial agents. In addition to its antimicrobial properties, silver is fairly biocompatible, is corrosion resistant and has good physical strength. Silver has been used in the form of organic salts, colloidal preparations, coatings and oxides, and by incorporating it into other materials such as being woven into polymers for use in sutures.

The mechanism of the antimicrobial activity of silver is not completely understood. The silver cation $Ag^+$ is a reactive chemical species that binds strongly to electron donor groups containing sulfur, oxygen or nitrogen. Bacterial cell surfaces—and biological molecules in general—contain all these elements in the form of thiol, amino, imidazole, carboxylate and phosphate groups. In addition, silver can also act by displacing other essential metal ions such as $Cu^{2+}$ or $Zn^+$. Despite the fact that silver ions have antimicrobial effects that are at least as high as other heavy metals, it is clear that the toxic effects of silver ions on mammals is considerably lower. The main adverse effect of prolonged exposure to high levels of silver is argyria, which is a gray or black discoloration in subcutaneous tissue which may be localized in areas such as the hands or eyes or generalized over the whole body. Argyria is irreversible and perhaps unpleasant, but is thought to be purely a cosmetic phenomena with no associated functional disorders.

Silver coatings have been used for their antimicrobial properties in a number of in-dwelling or implanted catheters and catheter-related devices. For example, studies have demonstrated reduced catheter-associated bacteriuria in the use of silver alloy coated catheters. See "Silver Alloy Coated Catheters Reduce Catheter-Associated Bacteriuria", British Journal of Urology (1990) 65, 379–81. Antimicrobial silver-coated catheters are described in U.S. Pat. Nos. 4,5692,920 by Murtfeldt, 4,564,361 by Akiyama and 4,483,688 by Akiyama. In U.S. Pat. No. 4,886,505 by Haynes, there is described an antimicrobial catheter that relies upon a plurality of metals.

It is believed that the vast majority of prior art on antimicrobial silver coatings for medical devices is in the field of implants or in-dwelling devices such as urinary catheters or other catheters or cannulation devices such as those mentioned above, while there is very little prior art on silver coatings for extracorporeal devices. For example, the Haynes patent mentioned above states:

> Preferred apparatuses in accordance with the invention are modified medical devices such as, for example, modified catheters, tracheal tubes, insulin pumps, would closures or drains, stopcocks, connectors, prosthetic devices, pacemaker leads, needles and the like. Most preferably, the apparatus of the invention remains in contact with the body for a period of time such that, without modification of the device surface in accordance with the invention, microorganism growth in association with the use of the device would occur. The most preferred apparatus of the invention is a modified catheter, in particular an indwelling urinary catheter.

The reason that antimicrobial silver coatings are largely limited to intracorporeal applications may be that until now the antimicrobial activity of the silver coatings were designed more to prevent on-going colonization than to act as a sterilant, and colonization occurs mainly in the colonization-conducive environment of inside the body rather than in a less-hospitable extracorporeal environment. Also, it has been thought that dissolution of the silver ions is important for effective antimicrobial activity, and dissolution occurs best in a liquid environment. See U.S. Pat. No. 4,886,505 by Haynes, mentioned above, and "Silver Accumulation in Pseudomonas Stutzeri AG259", Biology of Metals (1989) 2:168–173.

Other references in the field include U.S. Pat. Nos. 4,603,152 by Laurin, 5,049,139 by Gilchrist, 4,054,139 by Crossley and 4,559,033 by Stephen. The Laurin reference is fundamentally different from the present invention in that the surfaces coated with the antimicrobial agent are not guarded from touch contamination by any physical structure. Thus, the antimicrobial system depends entirely on the coating without any assistance from the configuration of the device. In the Gilchrist reference, the object is not to use an antimicrobial agent to prevent touch contamination of a connector surface, but to use the antimicrobial agent to sterilize contaminated fluid flowing through the connector. The Crossley and Stephen references are not concerned with antimicrobial agents applied to external connectors.

From the foregoing, it is clear that there is a need for an extracorporeal tubing connector that is simple and inexpensive to manufacture, easy to operate, and effective in preventing the transmission and not just colonization of microbes.

SUMMARY OF THE INVENTION

The present invention is an extracorporeal, releasable, antimicrobial tubing connector having particular but not exclusive application in peritoneal dialysis and hemodialysis tubing sets. The connector in a preferred embodiment includes a female portion which is attached to one tubing segment and a mating male portion that is attached to a joining tubing segment. The male portion includes a tubing attachment element on one end. The other end has a chamfered tubular member surrounded by an outer sleeve that is radially spaced from the tubular member. The radially inner surface of the sleeve is threaded. The female portion includes a tubular body, the inside of which receives the male tubular member. On the inside of the female tubular body may be an O-ring seal to seal against the male tubular member to result in a liquid-tight connection. The outer surface of the female tubular body is threaded to mate with the threads on the inner surface of the sleeve of the male portion. The outer surface of the female tubular body may also include a second O-ring to seal against the inner surface of the sleeve of the male portion as a secondary fluid barrier to make the connection liquid-tight.

An antimicrobial silver coating is applied to one or more of several surfaces, including: the outer surface of the female tubular body, the inner surface of the sleeve of the male portion, or the outer surface of the male tubular member. The connection is accomplished by inserting the male tubular member into the female tubular body, and then rotatingly engaging the threads on the inner surface of the sleeve of the male portion with the mating threads on the outer surface of the female tubular body. The mating of the threads draw the male and female portions together so that the outer surface of the male tubular member seals against the O-ring seal in the inner surface of the tubular female body, and the inner surface of the sleeve of the male portion seals against the O-ring seal on the outer surface of the tubular female body. A liquid-tight, and mechanically strong and secure connection is thus established.

The silver coating may be applied by various coating processes known in the art, including ion assisted deposition ("IAD"). In IAD coating, a thin film of silver is deposited from a vapor or sputtering source onto a substrate which is simultaneously bombarded with energetic ions to provide atomic rearrangements, resulting in a substrate that is both coated and impregnated with the film material.

DETAILED DESCRIPTION OF THE INVENTION

Figure 2:
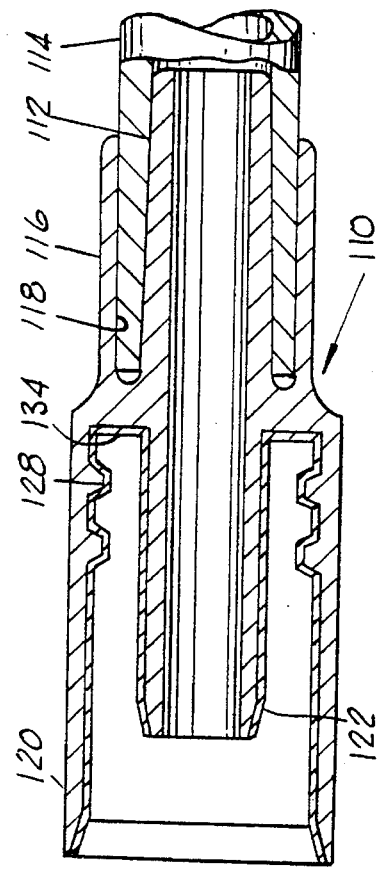
FIG. 2 shows a side sectional view of the male portion of the present invention, attached to a male tubing segment.
Figure 1:
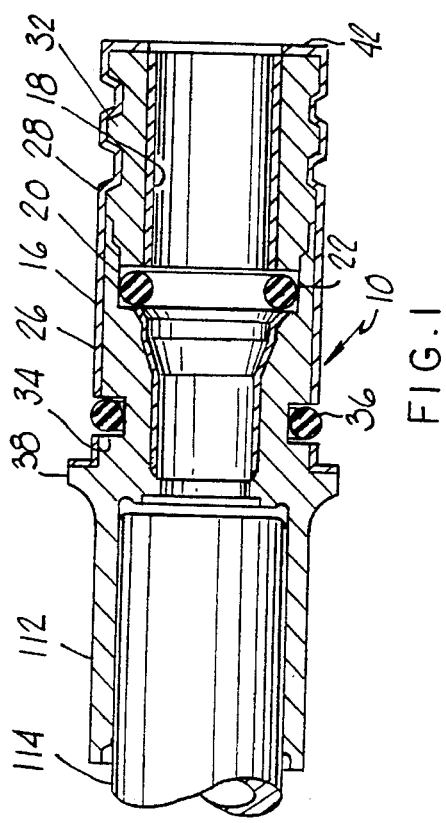
FIG. 1 shows a side sectional view of the female portion of the present invention, attached to a female tubing segment.

The female portion 10 and male portion 110 of a connector in accordance with the present invention are shown in FIGS. 1 and 2, respectively. The female portion 10 includes a flange 12 that is attached to the end of a tubing segment 14 to form a fluid-tight connection between the female portion 10 and the tubing segment 14. The attachment may be by a suitable adhesive, by ultrasonic welding or by any other attachment process known in the art.

The end of the female portion 10 opposite the flange 12 includes a hollow cylindrical shape which is referred to herein as a tubular body 16. Because the interior of the tubular body 16 is in communication with the inside of the flange 12, there is a continuous fluid pathway from the tubing segment 14 through the tubular body 16 of the female portion 10. The tubular body 16 includes a radially inner surface 18 which includes an annular notch 20. The annular notch 20 receives an Oring seal 22 having the function described below. The female portion 10 may be assembled from two pieces, a tubing end 26 and a non-tubing end 28, with the division between the two at the annular notch 20. Thus, the O-ring seal 22 can be seated into the annular notch 20 before the two pieces 26 and 28 are attached, and then the two pieces 26 and 28 are attached to one another to form a unitary element with the O-ring seal 22 permanently seated in the annular notch 20. Again, the attachment may be by any suitable means known in the art including adhesive or ultrasonic welding.

The radially outer surface of the tubular body 16 includes a set of threads 32. Also, a second annular notch 34 extends around the radially outer surface of the tubular body 16. The second annular notch 34 receives a second O-ring seal 36 which is installed by stretching the second O-ring seal 36 over the tubular body 16, and sliding it along the tubular body 16 until it pops into the second annular notch 34. Finally, there is an annular stop 38 between the second O-ring seal 36 and the flange 12.

The male portion 110 shown in FIG. 2 includes a central tube 112, one end of which inserts into a male tubing segment 114 and the other end 112 of which is chamfered. A tube cover 116 extends axially over a portion of the central tube 114, but is spaced radially apart from the central tube to define an annular cavity 118 to receive the male tubing segment 114. The central tube 112, central tube cover 116 and male tubing segment 114 are preferably dimensioned and configured such that a fluid-tight interference fit is established between the male portion 110 and the male tubing portion 114. The fit may be made doubly secure by an adhesive if desired.

Surrounding the central tube 112 on the end opposite the male tubing segment 114 is a sleeve 120 having a diameter such that an annular space is defined by the outer surface of the central tube 112 and the inner surface of the sleeve 120. The sleeve 120 preferably extends in the axial direction past the end of the central tube 112 so that the end 122 of the central tube 112 is recessed from the rim of the sleeve 120. On the radially inner surface of the sleeve 120 is a set of threads 128 that mate with the threads 32 of the female portion 10.

Figure 3:
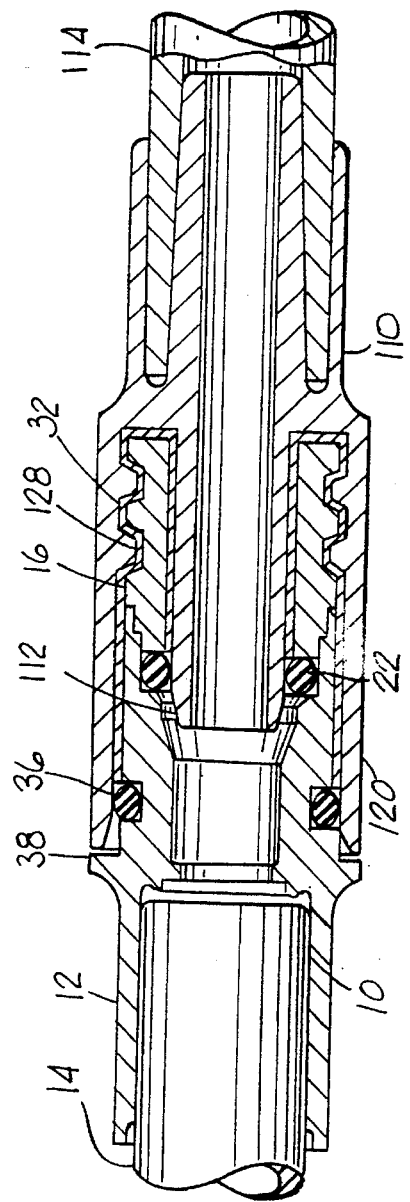
FIG. 3 shows the female portion of FIG. 1 and the male portion of FIG. 2 attached together.

The connection of the female portion 10 to the male portion 110 to establish fluid communication therethrough, is straightforward, and is shown in the assembly drawing of FIG. 3. The tubular body 16 of the female portion 10 receives the central tube 112 of the male portion 110, so that the central tube 112 fits inside the tubular body 16. This results in the outer surface of the central tube 112 of the male portion 110 being engaged with the first O-ring seal 22 which is on the inner surface of the tubular body 16 of the female portion 10. This results in a fluid-tight connection between the lumen of the female portion 10 and the lumen of the male portion 110.

At the same time, the tubular body 16 of the female portion 10 is situated in the space between the radially outer surface of the central tube 112 and the inner surface of the sleeve 120 of the male portion 110. The mechanical connection between the male portion 110 and the female portion 10 is achieved by the threading of the threads 32 of the female portion 10 with the threads 128 of the male portion 110. This simply requires that one of the male portion 110 and female portion 10 be rotated about its axis in relation to the other while a slight force is applied urging the two elements together. A second seal is established by the engagement of the second O-ring seal 36 with the inner surface of the sleeve 120 of the male portion. This second seal is redundant to the first seal (which is established by the engagement of the outer surface of the central tube 112 of the male portion 110 with the first O-ring seal 22) so that the overall connection is doubly fluid tight to resist leaking under internal pressure or upon wear of the seals after repeated use.

An antimicrobial silver coating is applied to at least one—and possibly several or even all—of certain surfaces. These surfaces are shown with a bold line in the drawings of FIGS. 1 and 2, and include: the radially outer surface of the tubular body 16 of the female portion 10, including the threads 32 thereof and optionally including the second O-ring seal 36; the end 42 of the tubular body 16 of the female portion; the radially inner surface of the tubular body 16 of the female portion 10 and optionally including the first Oring seal 22; the radially inner surface of the sleeve 120 of the male portion 110, including the threads 128 thereof; the wall 134 defining the end of the annular space between the sleeve 120 and the central tube 112 of the male portion 110; and the radially outer surface of the central tube 112 that is surrounded by the sleeve 120.

The surfaces most likely to become contaminated by touch in a manner that may pass the contamination onto the fluid flowing through the connection, are probably the radially inner and outer surfaces and end of the tubular body 16 of the female portion 10. It is this set of surfaces—and particularly the radially outer surface of the tubular body 16—which can easily be accidentally touched by a person or object. In contrast, the surfaces of the male portion 110 that are described above as candidates for an antimicrobial coating, are more difficult to reach to contaminate by touch. Thus, it is believed that it is the surfaces of the female portion 10 described above as candidates for an antimicrobial coating, that are most important for the coating. Of source, there is no limit to what surfaces can be coated on the male portion 110 and female portion 10. For example, one might wish to coat all the surfaces which come into contact with the fluid flowing through the connector such as the inner surface of the central tube 112 of the male portion.

The silver coating is preferably applied by an ion assisted deposition ("IAD") process. Such processes in general are known in the art, although it is believed that they have not previously been used in a device in the configuration described above. Briefly, IAD processes involve depositing a thin film onto a substrate from a vapor or sputtering source while the substrate and growing thin film is simultaneously bombarded with energetic ions to promote atomic re-arrangements. The process is performed in a high vacuum environment. Advantages of IAD coatings in the present application include good bactericidal properties, very little leaching, biocompatability, and little mineral encrustation. Also, the surface impregnation produced by IAD processes results in a coating that is flexible and highly resistant to flaking or chipping.

One of the significant ancillary benefits to the silver coatings is that they produce a very smooth, durable and low-friction surface. This aids in tightly engaging the threads 32 of the female portion 10 with the threads 128 of the male portion 10 and then disengaging the same.

Figure 4:
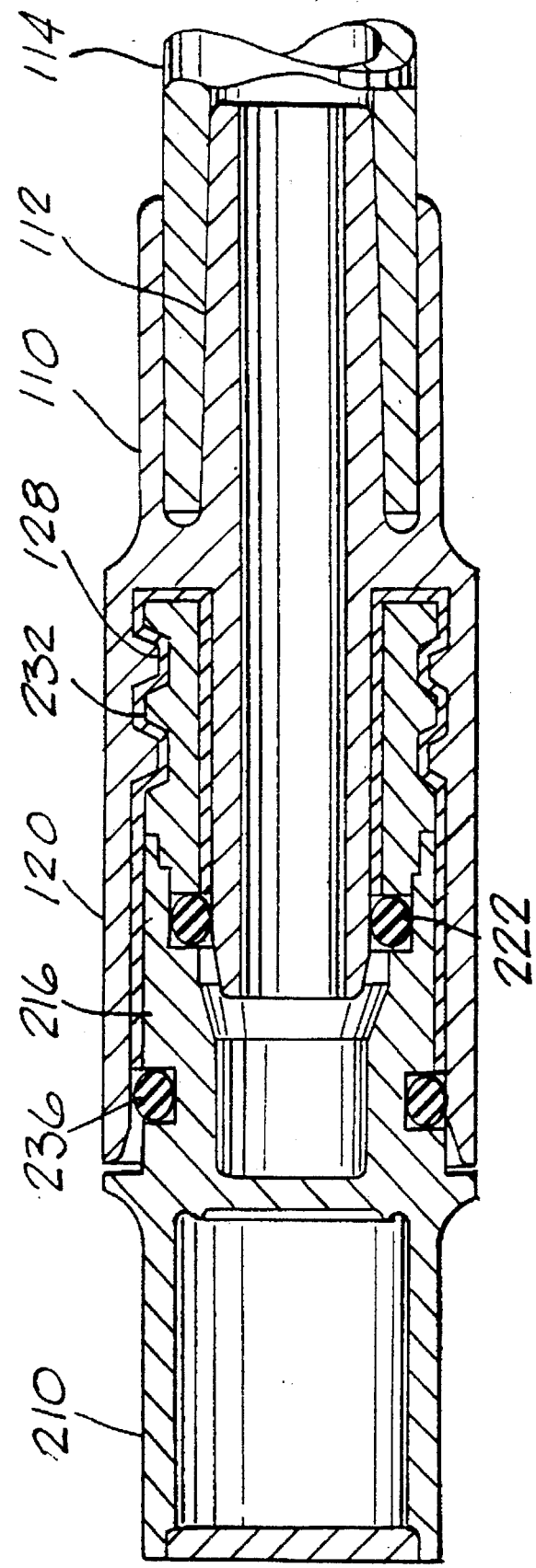
FIG. 4 is a side sectional view of the male portion of the present invention capped with a female cap.

FIG. 4 shows the male portion 110 of the present invention, and a female cap 210 in place of the female portion 10 of FIG. 3. The male portion 110 is essentially the same as the male portion 110 of FIGS. 2 and 3, with a central tube 112, a sleeve 120 surrounding the central tube 112 having a set of threads 128 on its radially inner surface. The male portion 110 is attached to a male tubing portion 114. The female cap 210 is similar to the female portion 10 of FIGS. 1 and 3, with a tubular body 216 having a set of threads 232 to engage the threads 128 on the male portion, an O-ring seal 222 on the radially inner surface of the tubular body 216, and a second O-ring seal 236 on the radially outer surface of the tubular body 216.

The female cap 210 of FIG. 4 differs from the female portion 10 of FIGS. 1 and 3, mainly in that the end opposite the end that mates with the male portion 110 is not attached to a female tubing segment such as the female tubing segment 14 of FIGS. 1 and 3. Instead, that end simply terminates, so that the female cap 210 functions as a cap to the male portion 110.

When the user is ready to use the connector, the female cap 210 of FIG. 4 is disconnected from the male portion 110 by unthreading the female cap threads 232 from the male portion threads 128. The female cap 210 may then be either discarded or saved for re-use. The male portion 110 is then connected to a female portion such as the female portions 10 of FIGS. 1 and 3 by threading the male portion threads 128 onto the female portion threads 32. This establishes fluid communication from the male tubing segment 114 through the connector to the female tubing segment 14. When the applicable medical procedure is completed, such as a peritoneal dialysis or hemodialysis treatment, the male portion 110 is disconnected from the female portion 10 by unthreading the female portion threads 32 from the male portion threads 128, and the male portion 110 is once again capped with the previously-removed or a new female cap 210.

Figure 5:
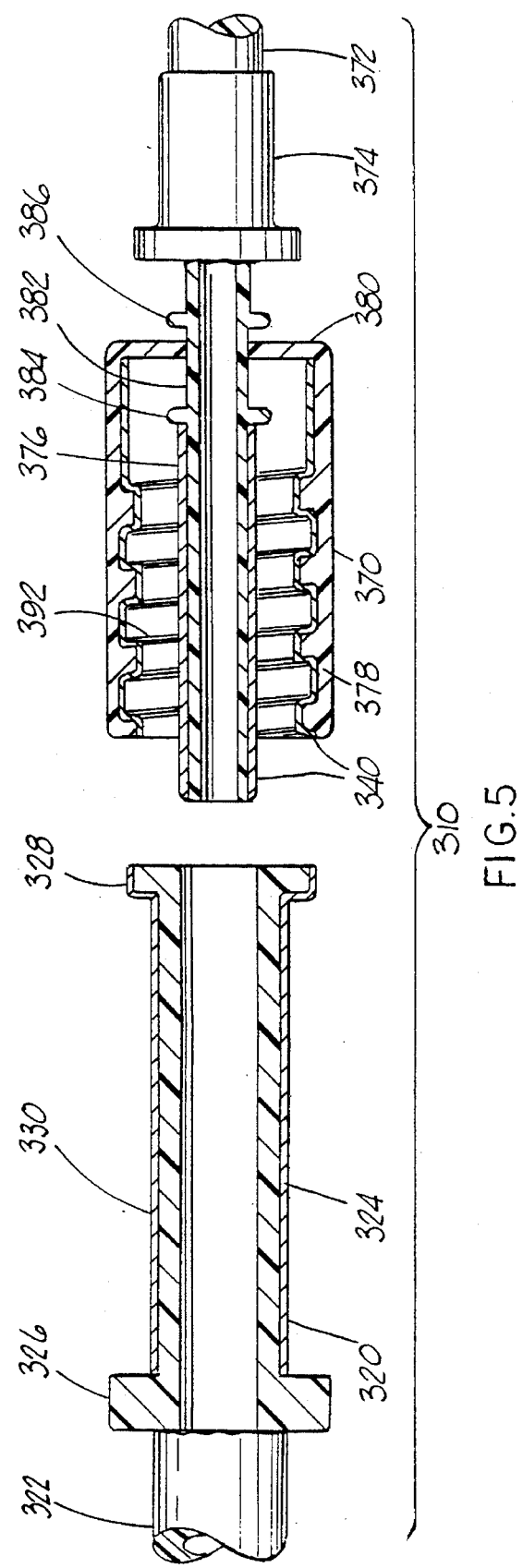
FIG. 5 is a side sectional view of the male and female portion of another embodiment of the present invention.

A variation of the invention for use with a typical hemodialysis connector is shown in FIG. 5. The connector 310 includes a female end 320 and a male end 370. The female end 320 is attached to a female tubing end 322 and includes a female tubular portion 324. The end of the female tubular portion 324 which abuts the female tubing end 322 has a shoulder 326 to allow the user to grasp the female end 320 effectively. The free end of the female end 320 has a set of radially protruding tabs 328. A bacteriocide silver coating 330 extends along the outer surface of the tubular portion 324, as shown, and may also include the same coating on the inner surface of the tubular portion 324.

The male end 370 of the connector 310 has one end that is attached to a male tubing end 372 by means of a tubing attachment 374. Attached to the tubing attachment 374 is a male tubular portion 376. Extending around the male tubular portion 376 is a collar 378 which is rotatable with respect to the male tubular portion 376. The rotation is accomplished by the collar end 380 being slidably mounted on a collar mount 382 of the male tubular portion 376 and retained on the male tubular portion 376 by a pair of collar stops 384 and 286. The radially inner surface of the collar 378 is threaded with a set of threads 392. A silver bacteriocide coating 390 is applied to the inner surface of the collar, including the threads 388 thereof and to the outer surface of the male tubular portion 376 as shown.

The male end 370 and female end 320 of the connector 310 are mated by sliding the male tubular portion 376 into the female tubular portion 324, so that the female tubular portion 324 is disposed between the male tubular portion 376 and the collar 378. This causes the tabs 328 of the female tubular portion 324 to engage the threads 392 of the collar 378. Rotating the collar 378 relative to the fixed male end 370 and female end 320 causes the collar 378 to shift longitudinally toward the female end 320 until the collar end 380 is stopped by the collar stop 384. At that point, further rotation of the collar 378 drives the male tubular portion 376 into the female tubular portion 324 to produce a snug and liquid-tight connection.

What is claimed is:

1. A connector for connecting and establishing fluid communication between a first tubing segment and a second tubing segment, the connector comprising: a first portion attachable to the first tubing segment, the first portion having a central tube with a radially inner surface for flowing a fluid therethrough, a radially outer surface and an end, and the first portion further having a sleeve extending around the central tube, the sleeve having a radially inner surface spaced radially apart from the central tube to define an annular space between the central tube and the sleeve; a second portion attachable to the second tubing segment, the second portion having a tubular body with a radially inner surface to receive said first portion central tube and a radially outer surface which is received by said, annular space; wherein an antimicrobial composition is on said radially inner surface of the central tube and said radially outer surface of the central tube, and at least one of said radially inner surface the sleeve, said radially inner surface of the tubular body, and said radially outer surface of the tubular body; the first portion being detachably attachable to the second portion whereby the first tubing segment may be placed in fluid communication with the second tubing segment; wherein said composition includes silver and is a coating applied by ion assisted deposition.

2. A connector for connecting and establishing fluid communication between a first tubing segment and a second tubing segment, the connector comprising: a first portion attachable to the first tubing segment, the first portion having a central tube with a radially inner surface for flowing a fluid therethrough, a radially outer surface and an end, and the first portion further having a sleeve extending around the central tube, the sleeve having a radially inner surface spaced radially apart from the central tube to define an annular space between the central tube and the sleeve; a second portion attachable to the second tubing segment, the second portion having a tubular body with a radially inner surface to receive said first portion central tube and a radially outer surface which is received by said annular space; wherein an antimicrobial composition is on said radially inner surface of the central tube and said radially outer surface of the central tube, and at least one of said radially inner surface the sleeve, said radially inner surface of the tubular body, and said radially outer surface of the tubular body; the first portion being detachably attachable to the second portion whereby the first tubing segment may be placed in fluid communication with the second tubing segment; and; a first O-ring seal positioned between the second portion and the first portion, wherein said first O-ring seal is on one of the radially outer surface of the central tube and the radially inner surface of the tubular body, sealingly engageable with the other of the radially outer surface of the central tube and the radially inner surface of the tubular body; and a second O-ring seal positioned between the second portion and the first portion further resulting a fluid-tight seal therebetween.

3. The connector of claim 2, wherein the second O-ring seal is on one of the radially outer surface of the tubular body and the radially inner surface of the sleeve, to sealingly engage the radially outer surface of the second portion tubular body and the radially inner surface of the sleeve.

4. A connector for connecting and establishing fluid communication between a first tubing segment and a second tubing segment, the connector comprising: a first portion attachable to the first tubing segment, the first portion having a central tube with a radially inner surface for flowing a fluid therethrough, radially outer surface and an end, and the first portion further having a sleeve extending around the central tube, the sleeve having a radially inner surface spaced radially apart from the central tube to define an annular space between the central tube and the sleeve; a second portion attachable to the second tubing segment, the second portion having a tubular body with a radially inner surface to receive said first portion central tube and a radially outer surface which is received by said annular space; wherein an antimicrobial composition is on said radially inner surface of the central tube and said radially outer surface of the central tube, and at least one of said radially inner surface the sleeve, said radially inner surface of the tubular body, and said radially outer surface of the tubular body; the first portion being detachably attachable to the second portion whereby the first tubing segment may be placed in fluid communication with the second tubing segment; and a cap for capping said first portion, the cap being attachable to the first portion and having a tubular body with a radially inner surface to receive said first portion central tube and a radially outer surface which is received by said annular space.

5. The connector of claim 4, wherein an antimicrobial composition including silver is on at least one of the radially inner surface of the cap tubular body and the radially outer surface of the cap tubular body.

6. A connector for connecting and establishing fluid communication between a first tubing segment and a second tubing segment, the connector comprising: a first portion attachable to the first tubing segment, the first portion having a central tube with a radially inner surface for flowing a fluid therethrough, a radially outer surface and an end, and the first portion further having a sleeve extending around the central tube, the sleeve having a radially inner surface spaced radially apart from the central tube to define an annular space between the central tube and the sleeve; a second portion attachable to the second tubing segment, the second portion having a tubular body with a radially inner surface to receive said first portion central tube and a radially outer surface which is received by said annular space; wherein an antimicrobial composition is on said radially inner surface of the central tube and said radially outer surface of the central tube, and at least one of said radially inner surface the sleeve, said radially inner surface of the tubular body, and said radially outer surface of the tubular body; the first portion being detachably attachable to the second portion whereby the first tubing segment may be placed in fluid communication with the second tubing segment; wherein the first portion includes a set of threads and the second portion includes a set of mating threads to threadably connect and disconnect the first portion and the second portion.

7. The connector of claim 6, wherein the radially outer surface of the tubular body includes a set of threads and the radially inner surface of the sleeve includes a set of mating threads.

* * * * *